United States Patent [19]

Noon et al.

[11] Patent Number: 5,049,393

[45] Date of Patent: Sep. 17, 1991

[54] ANTI-THROMBOGENIC ELASTOMER AND OBJECTS AND PROSTHESES MADE THEREFROM

[75] Inventors: George P. Noon; Louis W. Feldman, both of Houston; Julia A. Peterson, South Houston, all of Tex.

[73] Assignee: Baylor College of Medicine, Houston, Tex.

[21] Appl. No.: 213,760

[22] Filed: Jun. 30, 1988

Related U.S. Application Data

[63] Continuation of Ser. No. 816,927, Jan. 7, 1986, abandoned.

[51] Int. Cl.$^5$ .................................................. A61K 9/00
[52] U.S. Cl. .................................... 424/484; 424/487; 523/112; 523/113; 523/115
[58] Field of Search ..................... 523/112, 113, 115; 424/484, 487

[56] References Cited

U.S. PATENT DOCUMENTS

| | | | |
|---|---|---|---|
| 3,512,183 | 5/1970 | Sharp | 523/113 X |
| 3,526,005 | 9/1970 | Bokros | 424/424 |
| 3,708,324 | 1/1973 | Stebleton | 427/342 |
| 3,738,906 | 6/1973 | Olcott | 428/212 |
| 3,893,196 | 2/1976 | Hochman | 623/18 |
| 3,914,802 | 10/1975 | Reick | 623/1 |
| 3,916,892 | 11/1975 | Latham, Jr. | 604/83 |
| 3,936,887 | 2/1976 | Hodosh | 623/16 |
| 3,962,519 | 6/1976 | Rüsch et al. | 523/112 X |
| 3,963,677 | 6/1976 | Enger | 523/113 |
| 4,219,520 | 8/1980 | Kline | 264/129 |
| 4,281,991 | 8/1981 | Michl et al. | 523/115 |
| 4,303,596 | 12/1981 | Allen | 523/112 X |
| 4,552,148 | 12/1985 | Hardy | 606/154 |
| 4,595,713 | 6/1986 | St. John | 523/112 X |

FOREIGN PATENT DOCUMENTS 002931  7/1979  European Pat. Off. .
22253494 7/1975  France .

OTHER PUBLICATIONS

*Biocompatability of Clinical Implant Materials*, "Isotropic carbons used in clinical devices" 6–42, 1981, Haubold et al.
*Silicone*, Modern Plastics Encyclopedia, 113–115, 1975.
*Artificial Organs*, Parts 1 and 2, Chemical Engineering News, Apr. 1971.
Bently bioCarbon ® "Vascular Access System".
American Bentley, "Revolution in Vascular Access".
Petrarch Systems Inc. Catalog.
Cardiac Control Systems Inc. Letter and order form.
B. F. Goodrich, Estane ® polyurethanes, Product data sheets.

*Primary Examiner*—Thurman Page
*Assistant Examiner*—William E. Benston
*Attorney, Agent, or Firm*—Fulbright & Jaworski

[57] ABSTRACT

Disclosed are anti-thrombogenic compositions, methods for their production and products made therefrom. The Anti-thrombogenic compositions comprise a powderized anti-thrombogenic material homogeneously present in a solidifiable matrix material. The anti-thrombogenic material is preferably carbon and more preferably graphite particles. The matrix material is a silicon polymer, a urethane polymer or an acrylic polymer.

26 Claims, 3 Drawing Sheets

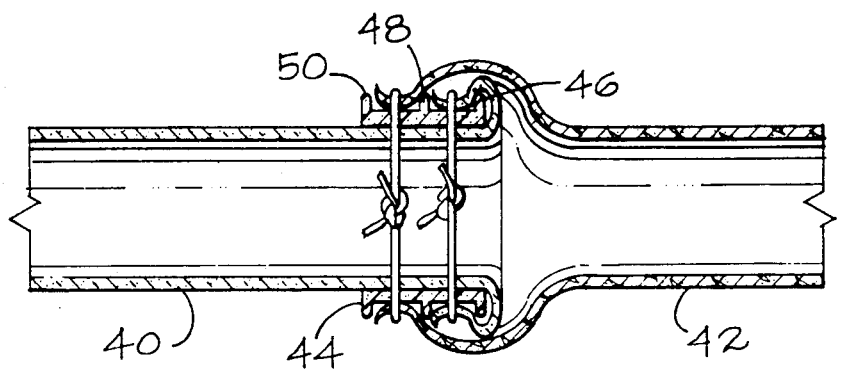
Fig. 3
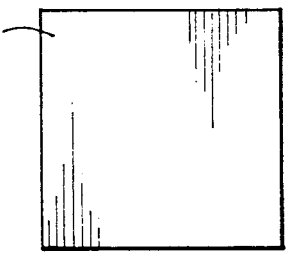
Fig. 4A
Fig. 4B
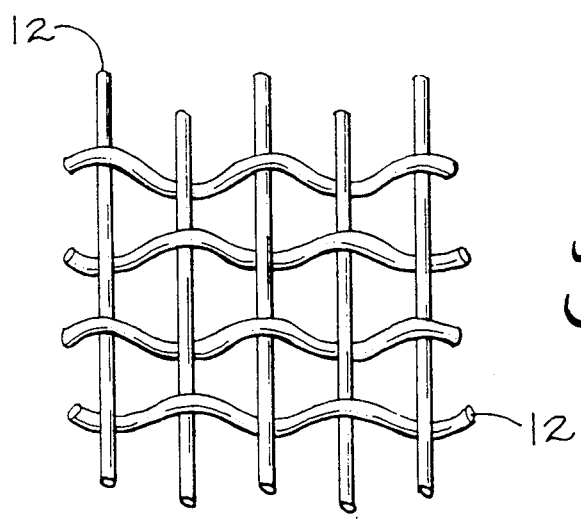
Fig. 5
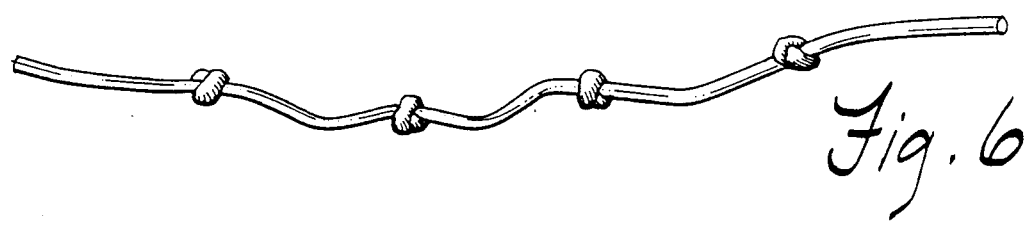
Fig. 6

ANTI-THROMBOGENIC ELASTOMER AND OBJECTS AND PROSTHESES MADE THEREFROM

This is a continuation of application Ser. No. 816,927, filed Jan. 7, 1986, abandoned.

BACKGROUND OF THE INVENTION

1. Field of the Invention

This invention is directed to anti-thrombogenic prostheses; to methods of making anti-thrombogenic prostheses; to anti-thrombogenic materials for use in making such prostheses; to methods for preparing such materials; to objects made form such materials other than prostheses which contact or come into contact with blood; and to surgical techniques for using such things.

2. Description of the Prior Art

Introduction

Prosthesis is the replacement of missing parts of animal bodies, including the human body, with artificial devices. As noted in the articles on "Artificial Organs" (Parts 1 and 2) which appear in the Apr. 5, 1971 issue of Chemical and Engineering News, the main problem encountered with such artificial devices, hearts and other organs as well as in human implants such as finger joints and synthetic plastic tubing serving as blood vessels, is the incompatibility of the prosthetic material with human blood. In order to be compatible with blood, that the prosthetic material must not cause blood clotting or bring about the destruction of red blood cells. The material must not alter blood proteins, cause damage to blood platelets, or produce other deleterious blood changes.

Although artificial materials in contact with blood can give rise to many adverse reactions, of greatest medical concern is the tendency of known materials to cause blood clots or thrombi. A material that has a marked tendency to induce clotting is referred to as highly thrombogenic. Thrombogenic materials are unacceptable because clots forming on their surface may dislodge and be carried along in the blood stream until they completely block a blood vessel, causing heart attack or stroke. If the clot remains at its formation site in a narrow organ such as a blood vessel, it can dangerously constrict the vessel. To be acceptable, a prosthetic material must satisfy a large number of critical requirements: it must be anti-thrombogenic; the material must not damage adjacent tissue; it must be free of carcinogenic or toxic agents; and it must not induce allergic reactions or interfere with the normal immunological mechanism of the body.

PRIOR ART PROSTHETIC MATERIALS

Metals, Plastics and Elastomers

In order to further the development and utilization of prosthetic devices, the surfaces of these devices which come in contact with blood and tissues should be completely compatible therewith, whether the contact be made by implantation or insertion within the body or by passage therethrough of blood at locations exterior of the body. Some of the most common materials for intravascular prostheses and artificial hearts and parts thereof are metals, plastics, and elastomers. Metals are used in applications requiring high strengths and good wearability. Plastics are used for applications wherein flexibility is needed. Metals are thrombogenic and are subject to corrosion. Plastics are thrombogenic and are subject to degradation. Stainless steel, titanium, and tantalum are among the most popular metals used today. Teflon (Reg. T.M.) and the polycarbonates are examples of plastics which have been used. None of these materials are satisfactory for prosthetic devices.

Another widely used prosthetic material is silicone rubber. This material is employed for implants and for various types of tubing to drain fluid from the brain, the chest cavity, the bladder and other organs. Silicone rubber, because of its flexibility, softness and other mechanical, biological and chemical properties, has distinct advantages. Silicone rubber promotes clotting when the blood is not flowing fast enough. Moreover, it does not possess sufficient strength when continuously flexed for protracted periods. Other problems with silicone include calcification and the leaching of chemical contaminants. Urethane is used as a prosthetic material, but it also causes calcification and clotting.

Synthetic polymers, such as "Dacron" polyester fiber are also in common use as a prosthetic material. Woven into a tight fabric, Dacron has found its greatest surgical use as artificial blood vessels and as patches for arteries and other human organs. While Dacron has good tensile and flexural strength and a high degree of compatibility with tissue, it can cause blood clotting in smaller vessels and arterial grafts. This tendency toward clotting is also characteristic of Teflon (polytetrafluoroethylene).

Electrets

Another factor which some investigators believe influences thrombogenicity is the electrical charge appearing on the surface of the prosthetic material. It is known that a negatively-charged or anionic substance is less prone to induce clotting than one which is positively-charged. The lining of natural blood vessels has a negative charge which is as high as 5 m V. This negative charge causes the lining to repel blood platelets and red blood cells whose surfaces are negatively-charged. The reason this charge repulsion is believed to inhibit blood clotting is that it prevents the attachment of platelets to the wall of the blood vessel. Such adhesion causes the platelet membrane to rupture and triggers off an intricate chain of enzyme activated steps that lead ultimately to the conversion of fibrinogen to fibrin. Fibrin is an insoluble protein that forms the matrix of a blood clot made up chiefly of fibrin, platelets and red blood cells. In an attempt to impart a negative charge to the surface of a prosthetic material in contact with blood so as to repel negatively-charged blood platelets, treated polymers called electrets have been developed. The polymers, after being heated to slightly below their melting point, are exposed to a strong electrical field. When the polymer cools, one side has a negative surface charge and the opposite side a positive charge. The difficulty with electrets is that they are not only costly and difficult to fabricate, but their electrical charge may decay, disappear or even reverse itself.

Pyrolytic Carbon Coatings

In an attempt to provide an outer surface, efforts have been made to coat a substrate with impervious isotropic pyrolytic carbon. In one form the carbon coating is a carbon film deposited by a carbon bearing gaseous precursor. The process requires low pressure and ambient temperatures. The coatings are less than 1 micron thick and can be deposited on most polymers, metals and ceramics. They have the following disadvantages:

1. The process is so expensive that it is not practical for most applications.
2. In order to coat the interior diameter of tubing, the tubing must be inverted. It is impossible to coat tubings of very small diameters, long lengths and moderately thick walls.
3. The coating can be penetrated and is therefore unsuitable for constantly flexed diaphragms.
4. The coating is relatively rigid and non-flexible.

Heparin-Receptive Surfaces

Heparin is an anti-coagulant. Efforts have been made to create Heparin-receptive surfaces on many types of formed plastic objections, particularly those formed from fluorinated hydrocarbons, through the use of a composition of matter comprising a mixture of a resin in particulate form and colloidal graphite. The mixture is processed into an object of predetermined size and shape by techniques such as extrusion, blow or injection molding, pressing and heating, or sheeting. The mixture can be formed into threads or yarns which can be braided, woven, knitted or felted into objects of predetermined size and shape. After an object has been formed from the mixture, its exposed surfaces preferably are treated with metallic sodium to expose surface areas of the colloidal graphite particles at or immediately underlying the exposed surfaces of the object, then the sodium treated surfaces are cleaned and coated with a cationic surface active agent to make the surfaces Heparin-receptive, after which a coating of Heparin may be applied over the cationic coating to make the object truly thrombo-resistant and non-thrombogenic. Although the compositions are particularly directed to those consisting of a mixture of particulate fluoropolymers and colloidal graphite, other materials in particulate form have been disclosed as possible replacements, such as halogenated hydrocarbons, polyolefins, polyurethanes, vinyls and silicones. Often this material fails to adhere properly and washes off.

Silica-Lined Multicomponent Layered Material

Attempts have been made to provide a prosthetic tubing having an inner layer of a non-thrombogenic substance which is bonded to and lines the face of a thin layer of oxygen-diffusing elastomeric material such as silicone or urethane rubber, the elastomeric layer being reinforced by a woven fabric backing made of synthetic plastic yarns of high-strength and acceptable chemical and biological properties. The resultant structure is similar in some respects to that of a fire hose in that the thin layer of rubber is externally-supported by fabric to provide a high-strength, burst-resistant tubing. The prosthetic tubing may be sutured, glued or otherwise connected to a vein or artery stub. The fabric backing is preferably woven of Dacron yarn, a polyester fiber made from polyethylene terephthalate. The porous Dacron permits diffusion to lock it into place after implantation. Also used as a backing is woven Lycra, made of a spandex fiber in the form of continuous monofilaments. This material causes clotting.

Gore-Tex (Reg. T.M.) Grafts

Gore-Tex (Reg. T.M.), which is primarily Teflon (Reg. T.M.), is used in vascular reconstructive surgery when the supply of autologous vein graft material is inadequate, usually because of length or diameter. Drawbacks of Gore-Tex include bleeding from suture holes and poor patency rates in 1 to 2 mm size. In addition, the high cost of Gore-Tex is a factor in the decision to use autologous veins whenever possible. Gore-Tex has poor ability to withstand repeated punctures and is not self sealing. The most serious defect in the Gore-Tex is that when it is punctured a hole is created in the wall of the graft. For this reason it is not acceptable for access devices such as access grafts for dialysis. This results in graft failure and frequent reoperations. It is very expensive and is not easily preformed into different shapes.

SUMMARY OF THE INVENTION

The present invention provides new anti-thrombogenic compositions of matter for forming objects, including prostheses, which come into contact with blood. Each of the new compositions includes an amount of very fine, powderized carbon such as graphite particles, ranging in size from about 3 to about 7 microns work well. The graphite particles are mixed with other materials ("matrix") to produce a composition with graphite present homogeneously throughout the material rather than present as colloidal graphite discretely interspersed in a material. The homogeneous presence of the fine graphite particles significantly increases the anti-thrombogenic nature of the resulting composition. Any matrix material can be used which can be mixed homogeneously with the graphite particles. Materials which can then be solidified, set, hardened, or cured ("solidifiable materials") are also useful according to this invention. In one form the composition can be poured into molds and the like to produce formed objects; for example, silicone, acrylics, and urethanes mix well with the graphite particles to form an anti-thrombogenic material. Bulk masses of the solidified material can be cut or shaped. When rubber or rubber-like matrix materials are used, a flexible product can be produced.

It is therefore an object of the present invention to provide an anti-thrombogenic composition.

Another object of the present invention is the provision of a method for preparing and making the new anti-thrombogenic composition.

Yet another object of the present invention is the provision of such a composition which can be used for prosthetic devices.

Still another object of the present invention is the provision of a method for making prosthetic devices from such a composition.

Particular objects of the present invention include the provision of and methods for: making a weaveable thread-like material; cloth; artificial heart valves; artificial arterial grafts; disposable diaphragm pumps and parts thereof for use outside the body; and artificial access grafts for hemodialysis made from the new composition.

Another particular object of the present invention is the provision of new sutures and surgical techniques for implanting prostheses made from the new composition.

Yet another object of the present invention is the provision of an anti-thrombogenic composition and method of preparation thereof which can be used to form objects with a self-sealing ability.

To one of skill in this art who has the benefit of this invention s teachings, other objects, features, and advantages will be apparent from the following descrip-

DESCRIPTION OF THE DRAWINGS

FIG. 3 is a cross-sectional view of the connection of an arterial graft according to the present invention to a natural artery.

FIG. 4A is a top plan view of a rectangular film according to the present invention.

FIG. 4B is a side view of the film of FIG. 4A.

FIG. 5 is a schematic view of a woven object according to the present invention.

FIG. 6 is a perspective view of a knotted suture according to the present invention.

DESCRIPTION OF THE PREFERRED EMBODIMENTS

Figure 1:
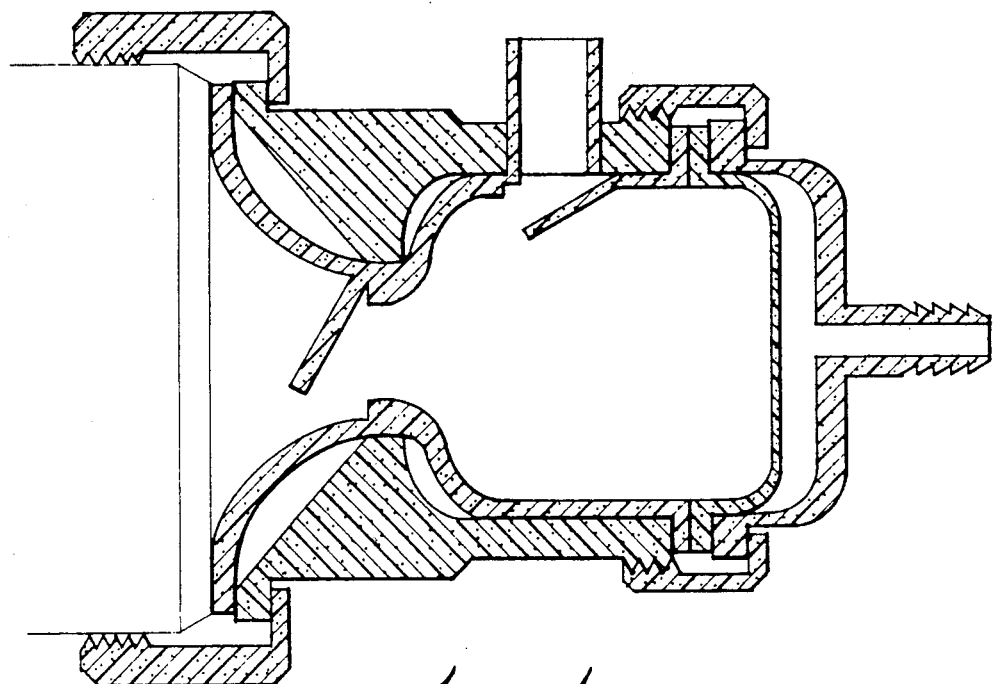
FIG. 1 is a cross-sectional view of a diaphragm pump for cardiopulmonary bypass surgery having parts made from a composition according to the present invention.

Although the preferred embodiments described here include powdered carbon in the form of graphite, it is to be understood that it is within the scope of the present invention to utilize any non-thrombogenic or anti-thrombogenic material in powdered form which can be homogeneously mixed with another material. Also, although the preferred embodiments described herein include materials such as silicones, acrylics and urethanes, it is to be understood that it is within the scope of the present invention to employ any miscible material which can be homogeneously mixed with powdered graphite and then used as in fluid form to create a mixture; in gel or gel-like form to create a mixture; or subsequently hardened, cured, or solidified either partially to form a flexible material or relatively more to form a more solid, less flexible material.

SAMPLE 1

17 grams of graphite were mixed with 408 grams of silicone and 50 grams of curing catalyst. The graphite used was powderized, the particles ranging in size from 3 to 7 microns (This particular powderized graphite was Southwestern Graphite Co.'s #1651. It is a mined mineral graphite.) The silicone was commercially available Dow Corning MDX44210 with its curing catalyst. The Dow Corning silicone is a clear to translucent, high strength silicone rubber which is essentially inert, has low shrinkage when cured at room temperature and is biocompatible. The base viscosity is 800 poises. The ingredients were stirred in a glass jar for a few minutes until the ingredients were homogeneously mixed together. The material was injected into molds and the molds with the mixed material were then cured in a curing oven for 1½ hours at 500° F.

SAMPLE 2

This was the same as Sample 1, but 1½ grams of the graphite were mixed with 50 grams of the silicone and 5 grams of catalyst.

SAMPLE 3

629 grams of the graphite used in Sample 1 were mixed with 619 grams of polyurethane (Estane ® 5714-F-1, one of a number of the Estane ® polyurethane resins supplied by B. F. Goodrich. The Estane ® polyurethane resins may be polyether or polyesters-based urethanes having a viscosity of 100–1200 cP.), 1 quart of tetrahydrofuran, a high hydrogen bond solvent/diluent for Estane (Reg. T.M.) polymers. These materials were homogeneously mixed in a glass container using a mixer for 2 hours. The material was introduced into molds and the molds were cured in a curing oven at 200° F. for 1½ hours.

SAMPLE 4

The mixture of Sample 3 was combined with the Dow Corning mixture of Sample 1 and stirred by hand for a few minutes in a glass jar until it was homogeneously mixed together. It was introduced into molds and the molds were cured in a curing oven at 250° C. for about 2 hours.

SAMPLE 5

539 grams of the urethane of Sample 3 were homogeneously mixed with 584 grams of the graphite of Sample 1 and 1000 ml of N,N, DimethylAcetamide ("DMAC"). The mixture was extremely viscous and 35 more grams of the urethane were added and mixed. The mixture was cured in molds in an oven at 200° F. for 2 hours.

SAMPLE 6

3 grams of the graphite of Sample 1 were homogeneously mixed with 50 grams of commercially available silicone A manufactured by Shin-Estu Chemical Co., Ltd. and available from Mitsui & Co. (U.S.A.), Inc. (Mitsui 1935) and 50 grams of commercially available silicone B manufactured by Shin-Estu Chemical Co., Ltd. and available from Mitsui & Co. (U.S.A.), Inc. (Mitsui 1935). Both silicone A and silicone B are transparent liquid silicone rubbers with viscosities of 750 and 450 poise. (Mitsui 1935). The material was then cured in an oven for 1 hour at 250° C.

SAMPLE 7

This sample was the same as Sample 6, but 4 grams of graphite were used. The results were similar.

SAMPLE 8

5 grams of commercially available Mitsui A (X-34-021) silicone was homogeneously mixed with 50 grams of commercially available Mitsui B (X-34-021) silicone and 3 grams of the graphite of Sample 1. This material was introduced into molds and the molds with the material were cured at 250° C. for 1 hour in a curing oven.

EXAMPLES 16 flexible tubular arterial grafts made from the material of Sample 4 were surgically inserted in 10 rats. 7 of these grafts remained patent (clear and open) longer than 1 hour. One of these grafts was patent at 6 days, but had clotting at 3 weeks. Of three grafts that were patent at 24 hours, one clotted at 4 days, one at 14 days, and one at 12 days. Three grafts were not patent at 24 hours. The grafts had an 0.8 mm internal diameter, and about 1.25 mm outer diameter. These grafts have a structure as shown by layer A of the tubular member P of FIG. 10.

A graft made from the material of Sample 4 having an internal diameter of 4 mm and a length of 4 cm was surgically inserted in the carotid artery of a goat. There was considerable bleeding around the suture sites with this graft. Upon sacrificing the animal the interior of the graft was found to be substantially patent with only a few specks of thrombus present. There was a large amount of organized thrombi outside around the external portion of the graft, but not adhering to the graft.

A flexible femoral arterial graft made from the material of Sample 6, 4 mm internal diameter and 5 cm long, was surgically inserted into the right femoral artery of a dog of about 14 Kg. At the same time another arterial graft made from Gortex (Reg. T.M.), 4 mm internal diameter and 5 cm long, was surgically inserted in the dog's left femoral artery. 6-0 prolene was used for suturing. At 30 minutes after insertion both grafts were patent. Bleeding around the graft according to the present invention was uncontrollable and clots were present within, but not adhered to, the graft.

Flexible tubular arterial grafts of 1 mm internal diameter and 4 mm internal diameter were made with the material of Sample 6. They were cured in a curing oven at a vacuum of 23 inches of mercury and at temperature of 200° C. for 1½ hours. The cured grafts were cleaned in a Bransonic 220 ultrasonic cleaner for 30 minutes using deionized water. They were stored in glass tubes and introduced into an oven at 250° C. for 3 hours.

Five flexible tubular grafts of 4 mm internal diameter with a wall thickness of 0.008 inches were made from the material of Sample 7. Two grafts of 4 mm internal diameter with a wall thickness of 0.010 inches were made from the same material. These were introduced into a curing oven at a recirculating temperature of 600° F. in glass tubes for 3 hours. The total curing time in the oven was 4 hours. These were implanted in a dog's femoral artery. They became clotted at the anastomosis sites, but the clots did not adhere to the wall of the graft.

Flexible tubular grafts were made from the material of Sample 7 which were 4 mm internal diameter, with a wall thickness of 0.025 inches. They were tested to 1000 mm Hg inner pressure without rupture. These grafts tore easily when punctured by a needle. To combat tearing, 7.0 Tycron (Ref. T.M.) silicone treated polyester suture was wrapped around the grafts. They were then put into a mold and silicone was injected into the mold surrounding the graft to provide a new silicone covering for the graft.

Another group of flexible tubular grafts were made with the material of Sample 7 which were 4 mm internal diameter with a 0.025 inch wall thickness. They were put into an oven at 250° C. for 30 minutes and, after removal from the oven, were wrapped with surgical gauze. A layer of silicone was applied to the gauze and then the grafts were placed again in the oven at 250° C. for 30 more minutes.

Both the Tycron (Reg. T.M.) reinforced grafts and surgical gauze reinforced grafts were surgically implanted in the femoral arteries of a dog. This time there was no excessive bleeding at the suture points. After 13 days both grafts were clotted at anastomosis sites, but no clots were adhered to the wall of the grafts.

Grafts made from the material of Sample 7, 4 mm internal diameter and having a wall thickness of 0.025 inches and with a layer of gauze and of silicone as described above, were surgically inserted into the femoral and carotid arteries of a dog. Upon removal thirteen days later, it was noted that there was tissue in-growth into the graft. Thrombi were lightly attached at the suture sites and had also travelled unattached through the graft to become lightly attached at subsequent suture sites. All the grafts were extremely stiff.

Flexible tubular grafts of 3½ mm internal diameter and a wall thickness of 0.020 inches were made from the material of Sample 8. Two of these grafts were implanted in a dog's femoral arteries and one in its carotid artery. There were no problems with the suturing and the grafts did not tear easily. Twenty-two days later one of the femoral artery grafts had torn away. The graft in the carotid artery had thrombus at the anastomosis sites along the graft length. There was no adherence of clots to the graft surface.

Figure 2:
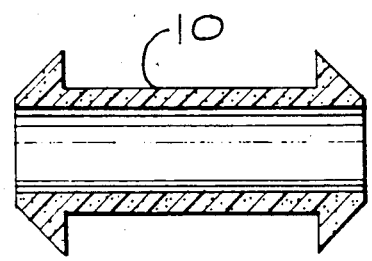
FIG. 2 is a cross-sectional view of a quick connect device according to the present invention

Often to connect the severed ends of a tubular such as an artery a "quick connect" coupling is used. As shown by the quick connect 10 in FIG. 2 solid hardened quick-connects can be made from a composition according to the present invention. The composition included about 1 gram of the graphite of Sample 1 homogeneously mixed with 22 grams of polymethacrylate [Fastcure (T.M.) acrylic produced by Kerr Company was used].

Thin flexible solid strands 12 of the invention's composition which are thread-like and weaveable can be woven into a cloth as depicted in FIG. 5.

Rectangular flexible thin films 14 have been made as illustrated in FIGS. 4A and B, 6 inches wide and 6 inches long, from the material of Sample 2. These films can be used to form containers, envelopes and bladders. The envelopes are useful for enveloping implants, such as breast implants. Also integral envelopes and bladders can be molded from the material. Solid prostheses such as artificial joints and bones or bone parts can also be made from the composition according to the present invention.

Rubber and rubber-like materials, e.g., silicones, exhibit a self-sealing characteristic which is very valuable in instances in which an object must be punctured such as by a needle. For example many hemodialysis grafts receive numerous needle insertions. The addition of graphite to silicone reduces or eliminates the silicone's self-sealing ability. To preserve this characteristic in objects made from compositions according to the present invention, a dual layer, multi-layer, or graded layer structure can be fashioned. As shown in FIGS. 9 and 10 a layer of material A according to the present invention can be used for the surface which will be in contact with blood so that the anti-thrombogenic effects of the material will be utilized. A second layer B of silicone (or other rubber or rubber-like, self-sealing material) is adhered to the first layer, thereby giving the object the self-sealing ability. In another embodiment (see FIGS. 7 and 8), powdered anti-thrombogenic material C is homogeneously present in the material at and near the surface to contact the blood and its content is gradually reduced in the region D towards the other surface E so that at the other surface E the self-sealing ability is maintained.

Figure 7:
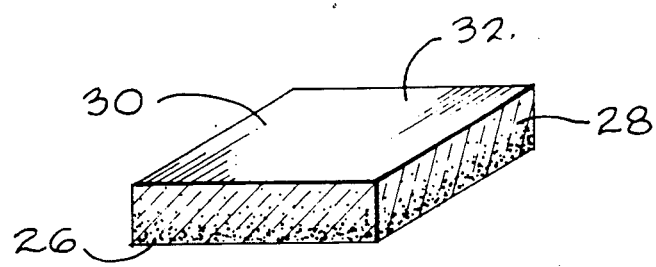
FIG. 7 is a schematic perspective depiction of a piece of material according to the present invention.
Figure 8:
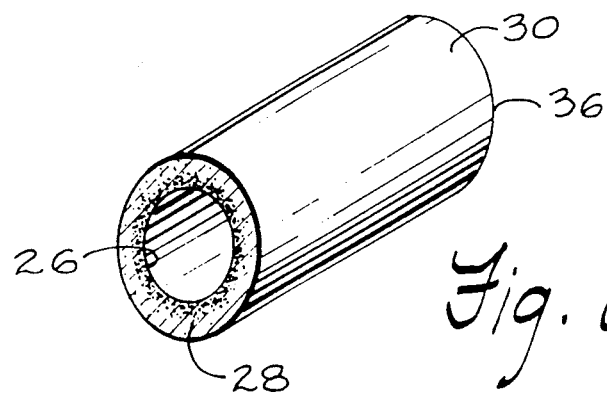
FIG. 8 is a schematic perspective depiction of a tubular member according to the present invention.
Figure 9:
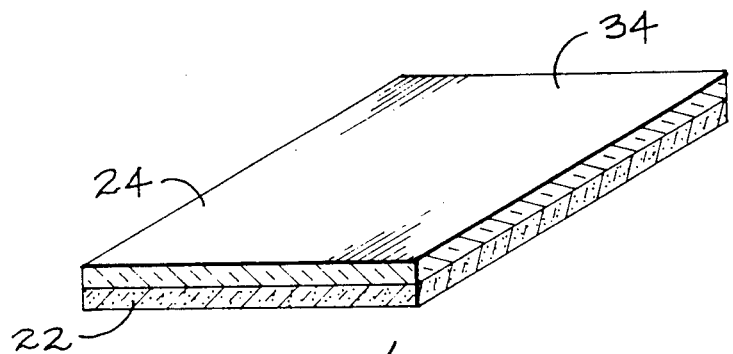
FIG. 9 is a schematic perspective depiction of a piece of material according to the present invention.
Figure 10:
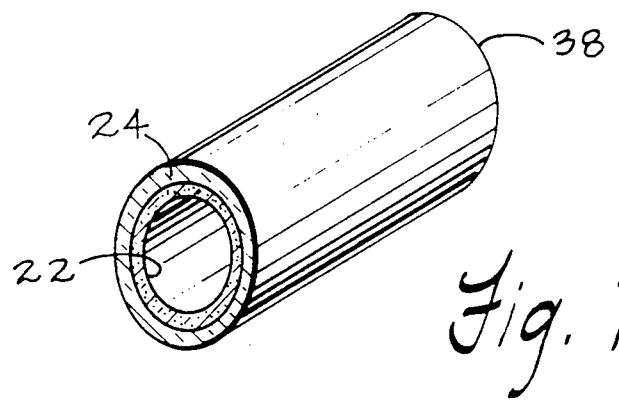
FIG. 10 is a schematic perspective depiction of a tubular member according to the present invention.

As shown in FIGS. 7 and 9, the material according to the present invention can be in the form of a sheet (M, N) or, as shown in FIGS. 8 and 10, it can be in the form of a tubular member (O, P). Of course, objects can be made from the composition according to the present invention in any desired shape or configuration. The objects, for example, can be made by pouring an amount of uncured or unhardened material into a mold or by working a piece of hardened or cured material. For example, the various parts of the diaphgram pump shown in FIG. 1 can be made from material according to the present invention. (This pump is disclosed in pending U.S. application Ser. No. 707,255.)

Any object which must contact blood can be fashioned from the material according to the present invention such as artificial heart valves (e.g., the pericardinal heart valves produced by Mitral medical of Canada, Ltd.; the prosthesis of U.S. Pat. No. 4,397,049; the items disclosed in the prior art in said patent; blood transfer, analysis or centrifugation systems and anastomotic devices as disclosed in U.S. Pat. No. 4,552,148 and the prior art disclosed in said patent.

FIG. 3 illustrates a surgical procedure and various apparatuses for connecting the tubular graft R according to the present invention to the natural artery S. The graft R is inserted through the ring T. An overlapping portion of the graft R is pulled back over the leading raised edge U of the ring T and tied with a suture about the recess formed between the edge U and the flange V. The tie ring T can be made from the composition according to the present invention. The natural artery S is emplaced about the R-T combination and is tied by suture about the ring T in the recess between the flange V and the trailing edge W.

In order to prevent the death of the tissue in the recess between the suture and the edge W, a knotted suture as shown in FIG. 6 can be used. Such a suture allows for an adequately tight tie, but also permits sufficient communication between tissue on either side of the tie so that the tissue between the tie and the edge W does not deteriorate and die.

In conclusion, therefore, it is seen that the present invention and the embodiments disclosed herein are well adapted to carry out the objectives and obtain the ends set forth. To one of skill in this art who has the benefits of this invention's teachings it will be clear that certain changes can be made in the methods and apparatuses without departing from the spirit and scope of the invention as defined in the following claims:

What is claimed is:

1. An antithrombogenic composition consisting essentially of
   a biocompatible miscible matrix material selected from the group consisting of a silicone polymer, an acrylic polymer and a urethane polymer, and
   powderized graphite distributed throughout said miscible material rendering said composition anti-thrombogenic throughout.

2. An antithrombogenic composition comprising
   a biocompatible miscible matrix material selected from the group consisting of a silicone polymer, an acrylic polymer and a urethane polymer, and
   powderized graphite particles ranging in size from about 3 to about 7 microns distributed throughout said miscible material rendering said composition anti-thrombogenic throughout.

3. An anti-thrombogenic composition comprising,
   miscible solidifiable material, the miscible solidifiable material selected from the group consisting of a silicone polymer, a urethane polymer and an acrylic polymer,
   powderized graphite particles ranging in size between about 3 to about 7 microns,
   said powderized graphite homogeneously distributed throughout said miscible material rendering said composition anti-thrombogenic throughout.

4. A process for preparing a homogeneous anti-thrombogenic composition consisting essentially of
   mixing a miscible material containing a polymer selected from the group consisting of a silicone polymer, an acrylic polymer and a urethane polymer, and powderized graphite.

5. The process of claim 4 wherein the miscible material is solidifiable.

6. The process of claim 5 wherein the solidifiable material is selected from the group consisting of a silicone polymer, urethane polymer, and an acrylic polymer.

7. The process of claim 4 wherein the anti-thrombogenic material is carbon.

8. The process of claim 7 wherein the anti-thrombogenic material is graphite particles.

9. A process for preparing a homogeneous anti-thrombogenic composition comprising
   mixing a miscible material containing a polymer selected from the group consisting of a silicone polymer, an acrylic polymer and a urethane polymer, and powderized graphite wherein said graphite comprises particles ranging in size from about 3 to about 7 microns.

10. The process of claim 4, including the step of solidifying the resulting mixture.

11. The process of claim 6 including the step of curing the solidifiable material.

12. A surgical process for connecting an artificial tubular graft to a natural tubular member, the process comprising,
    inserting the artificial tubular graft through an opening in a cylindrical hollow tie ring so that part of the artificial graft extends beyond the opening,
    folding back the extending part of the artificial graft over an outwardly extending front edge of the tie ring into a first recess between the front edge and a flange extending exteriorly from the middle of the tie ring,
    securing the folded back portion of the artificial graft in the first recess,
    introducing the artificial-graft-tie-ring structure into the natural tubular member so that the natural tubular member covers the first recess and extends beyond it into a second recess formed between the flange and an upwardly extending rear edge of the tie ring, and
    securing the natural tubular member in the second recess.

13. The process of claim 12 wherein the artificial tubular graft is an arterial graft and the natural tubular member is a bodily artery.

14. The process of claim 12 wherein the arterial graft is made from the composition of claim 1.

15. The process of claim 12 wherein the arterial graft is made from the composition of claim 3.

16. The process of claim 12 wherein a tied suture is used to secure the portions in the first and second recesses.

17. The process of claim 12 wherein a suture with knots spaced along its length is used to tie the natural tubular member in the second recess.

18. A tie ring for connecting a tubular graft to a natural tubular member, the tie ring comprising a hollow cylindrical body member having outwardly extending edges formed integrally at each end thereof and an outwardly extending flange formed integrally thereof between the two edges.

19. The tie ring of claim 18 formed of the composition of claim 1.

20. The tie ring of claim 18 formed of the composition of claim 3.

21. An anti-thrombogenic composition comprising,
a homogeneous mixture of a miscible solidifiable material selected from the group consisting of silicone, urethane and acrylic, and
powderized graphite particles ranging in size from about 3 to about 7 microns.

22. The composition of claim 1 wherein said solidifiable material comprises at least two materials selected from the group consisting of a silicone polymer, a urethane polymer and an acrylic polymer.

23. An object made from the composition of any one of claims 1, 2, 3, 4–11, 21 or 22.

24. The object of claim 23 wherein said object is a prosthetic device.

25. The object of claim 23 wherein said object is a tubular arterial graft.

26. The object of claim 23 wherein said object is a bladder.

* * * * *